(12) United States Patent
Berney-Smith (10) Patent No.: US 10,183,184 B2
(45) Date of Patent: Jan. 22, 2019

(54) CLOSED CIRCUIT BREATHING APPARATUS AND METHOD OF OPERATING SAME

(75) Inventor: Marcus Berney-Smith, Morpeth (GB)

(73) Assignee: DRAEGER SAFETY UK LIMITED, Blyth, Northumberland (GB)

(*) Notice: Subject to any disclaimer, the term of this patent is extended or adjusted under 35 U.S.C. 154(b) by 1044 days.

(21) Appl. No.: 14/241,724

(22) PCT Filed: Aug. 30, 2012

(86) PCT No.: PCT/GB2012/052126
§ 371 (c)(1),
(2), (4) Date: Apr. 22, 2014

(87) PCT Pub. No.: WO2013/030575
PCT Pub. Date: Mar. 7, 2013

(65) Prior Publication Data
US 2014/0261411 A1    Sep. 18, 2014

(30) Foreign Application Priority Data
Sep. 1, 2011 (GB) .................... 1115075.2

(51) Int. Cl.
*A62B 9/00* (2006.01)
*A61M 16/00* (2006.01)
(Continued)

(52) U.S. Cl.
CPC .......... *A62B 9/006* (2013.01); *A61M 16/0045* (2013.01); *A61M 16/0051* (2013.01);
(Continued)

(58) Field of Classification Search
CPC ...... A62B 9/006; A62B 7/02; A61M 16/0891; A61M 16/0045; A61M 16/0051; A61M 16/1075; A61M 2016/0027; A61M 2016/1025; A61M 2205/3606; A61M 16/024; A61M 16/0078
See application file for complete search history.

(56) References Cited

U.S. PATENT DOCUMENTS 4,440,166 A * 4/1984 Winkler .................. A62B 7/10
128/202.22
4,809,691 A    3/1989 Paole et al.
(Continued)

FOREIGN PATENT DOCUMENTS

CN    1621794    6/2005
CN    101180100    5/2008
(Continued)

OTHER PUBLICATIONS

English Translation of Search Report dated May 20, 2015 from corresponding Chinese Application No. 2012800427557.
The International Search Report dated Jan. 9, 2011.

*Primary Examiner* — Gregory Anderson
*Assistant Examiner* — Jonathan Paciorek
(74) *Attorney, Agent, or Firm* — DLA Piper LLP (US)

(57) ABSTRACT

A closed circuit breathing apparatus (2) and a method of operating the same, the method comprising: determining whether a sufficient amount of replenishing gas is being supplied to a breathing circuit (4); sensing pressure within the breathing circuit (4) using a pressure sensor (6); generating a pressure signal representative of the sensed pressure; determining whether the pressure signal is representative of breathing; and generating an alert if it is determined that both an insufficient amount of replenishing gas, such as oxygen, is being supplied to the breathing circuit (4) and that the pressure signal is representative of breathing.

20 Claims, 5 Drawing Sheets

(51) Int. Cl.
*A61M 16/08* (2006.01)
*A62B 7/02* (2006.01)
*A61M 16/22* (2006.01)
*A61M 16/10* (2006.01)

(52) U.S. Cl.
CPC ...... *A61M 16/024* (2017.08); *A61M 16/0891* (2014.02); *A62B 7/02* (2013.01); *A61M 16/0078* (2013.01); *A61M 16/1075* (2013.01); *A61M 16/22* (2013.01); *A61M 2016/0027* (2013.01); *A61M 2016/1025* (2013.01); *A61M 2202/0208* (2013.01); *A61M 2205/18* (2013.01); *A61M 2205/3606* (2013.01)

(56) References Cited

U.S. PATENT DOCUMENTS

| | | | |
|---|---|---|---|
| 5,072,728 A | 12/1991 | Pasternack | |
| 5,315,988 A | 5/1994 | Clarke et al. | |
| 6,672,300 B1* | 1/2004 | Grant | A61M 16/00 128/204.21 |
| 6,712,071 B1* | 3/2004 | Parker | A62B 7/02 128/201.25 |
| 2002/0195105 A1* | 12/2002 | Blue | A61M 16/00 128/204.21 |
| 2003/0213490 A1 | 11/2003 | Righetti | |
| 2006/0086357 A1 | 3/2006 | Soliman et al. | |
| 2006/0201509 A1* | 9/2006 | Forsyth | A62B 7/08 128/204.26 |
| 2009/0114223 A1 | 5/2009 | Bonassa et al. | |
| 2010/0012124 A1* | 1/2010 | Deas | A62B 9/006 128/204.22 |

FOREIGN PATENT DOCUMENTS

| | | |
|---|---|---|
| DE | 39 30 362 | 3/1991 |
| GB | 2 433 445 | 6/2007 |
| GB | 2460296 | 12/2009 |
| WO | 2004/105884 | 12/2004 |

\* cited by examiner

CLOSED CIRCUIT BREATHING APPARATUS AND METHOD OF OPERATING SAME

The invention relates to a closed circuit breathing apparatus and method of operating the same, and is particularly, although not exclusively, concerned with a closed circuit breathing apparatus used in portable personal protection systems.

Closed circuit breathing apparatus (CCBA) devices, which are often known as rebreathers, are used in environments in which the atmosphere is unsuitable for normal breathing. For example, CCBAs are often part of personal protection systems worn by rescue workers when working in hazardous environments, such as smoke-filled environments, in which the atmosphere is unsuitable for breathing.

A CCBA generally comprises a breathing circuit having a breathing port, a counterlung (or breathing bag), a carbon dioxide absorber, such as a scrubber, and a cooler. A cylinder of oxygen is provided for supplying oxygen to the breathing circuit.

During use, air is inhaled and exhaled through the breathing port so that gas is continually re-circulated in a closed breathing circuit, rather than being released into the atmosphere. As the user inhales and exhales, oxygen within the re-circulated air is consumed by the user and carbon dioxide is generated by the user. The oxygen consumed by the user is replenished by the oxygen supply and carbon dioxide is removed by the carbon dioxide absorber. The amount of oxygen and carbon dioxide contained in the circulated air is therefore maintained at levels which ensure that the user can breathe safely.

It should be appreciated that although the above devices are commonly referred to as "closed circuit breathing apparatus" devices, the breathing circuit is not completely closed. During use, oxygen is added to the breathing circuit and some recirculated air is allowed to vent to the atmosphere. However, a substantial proportion of the exhaled air is recirculated within the breathing circuit, hence the use of the term "closed circuit".

A problem associated with conventional CCBAs is that a user can breathe through the CCBA even when no, or insufficient, oxygen is being supplied to the breathing circuit. This may occur if the valve associated with the cylinder of oxygen has not been correctly opened. In such circumstances, oxygen is not supplied to the breathing circuit and therefore the oxygen content of the re-circulated air falls. If the user fails to notice this, this may lead to gradual suffocation of the user. This places the user at significant risk.

It is therefore desirable to provide CCBA devices with an alert system for alerting a user that oxygen is not being supplied to the breathing circuit. In order to ensure that an alert is only generated when the user is attempting to breathe through the breathing circuit, the CCBA is also equipped with a pressure switch which is activated by pressure changes within the breathing circuit. An alert is only generated when the pressure within the breathing circuit reaches a threshold value, and it is determined that insufficient oxygen is being supplied to the breathing circuit.

Pressure switches are unable to distinguish between pressure changes caused by relatively small fluctuations in the ambient pressure, for example as a consequence of temperature fluctuations or disturbances in the vicinity of the CCBA, and fluctuations caused by breathing. Therefore, in order to prevent false alarms caused by the small fluctuations in the ambient pressure, the sensitivity of the pressure switches must be reduced. However, reducing the sensitivity of the pressure switches increases the risk that breathing, for example shallow breathing, will go undetected. Consequently, a user breathing through the CCBA may not always be alerted to an insufficient supply of oxygen. This is undesirable.

In a broad aspect the invention relates to a method of sensing a pressure signal within a breathing circuit and determining whether the pressure signal is representative of breathing.

According to a first aspect of the present invention there is provided a method of operating a closed circuit breathing apparatus having a breathing circuit, the method comprising: determining whether a sufficient amount of replenishing gas is being supplied to the breathing circuit; sensing pressure within the breathing circuit using a pressure sensor; generating a pressure signal representative of the sensed pressure; determining whether the pressure signal is representative of breathing; and generating an alert if it is determined that both an insufficient amount of replenishing gas is being supplied to the breathing circuit and that the pressure signal is representative of breathing.

The replenishing gas may be oxygen which may be supplied from an oxygen cylinder.

It may be determined that the pressure signal is representative of breathing when the pressure signal comprises the characteristics of at least one inhalation event and at least one exhalation event within a predetermined period.

It may be determined that the pressure signal is representative of breathing when the pressure signal comprises the characteristics of at least two inhalation events and/or at least two exhalation events within the predetermined period.

It may be determined that the pressure signal is representative of breathing when the pressure signal sequentially comprises the characteristics of an inhalation event, an exhalation event, and an inhalation event within the predetermined period; or when the pressure signal sequentially comprises the characteristics of an exhalation event, an inhalation event, and an exhalation event within the predetermined period The predetermined period may be at least one tenth of a second, and may be at least two seconds. The predetermined period may be less than 10 seconds, or less than 8 seconds, for example.

It may be determined that the pressure signal comprises the characteristics of an inhalation event or an exhalation event when the pressure signal is indicative of a pressure change within the breathing circuit which corresponds to a depth of breathing which is at least 0.5 liters, or at least one liter.

It may be determined that the pressure signal comprises the characteristics of an exhalation event when the magnitude of the pressure signal exceeds an upper threshold, and it may be determined that the pressure signal comprises the characteristics of an inhalation event when the magnitude of the pressure signal falls below a lower threshold.

It may be determined that the pressure signal is representative of breathing when the pressure signal sequentially comprises a first pressure change that exceeds a pressure change threshold, a second pressure change that exceeds a pressure change threshold, and a third pressure change that exceeds a pressure change threshold. The first and third pressure changes may be pressure rises and the second pressure change may be a pressure fall. The first and third pressure changes may be pressure falls and the second pressure change may be a pressure rise. It may be determined that the pressure signal is representative of breathing when the second pressure change occurs within a preset time window following the first pressure change and when the third pressure change occurs within a preset time window following the second pressure change.

According to a second aspect of the present invention there is provided a closed circuit breathing apparatus comprising: a breathing circuit; a replenishing gas sensor for determining whether a sufficient amount of replenishing gas is being supplied to the breathing circuit; a pressure sensor arranged to sense pressure within the breathing circuit, the pressure sensor being arranged to output a pressure signal which is representative of the sensed pressure; and a controller connected to the pressure sensor, the controller being arranged to determine whether the pressure signal is representative of breathing and to generate an alert if it is determined that both an insufficient amount of replenishing gas is being supplied to the breathing circuit and that the pressure signal is representative of breathing.

The breathing circuit may comprise a carbon dioxide removal unit, a variable volume breathing bag (counterlung) and a cooler that are in fluid communication with one another. The breathing apparatus may comprise a mouthpiece in fluid communication with the breathing circuit and may comprise first and second one-way valves such that gas can only flow within the breathing circuit in one direction. An oxygen supply, such as a cylinder of oxygen, may be provided to supply oxygen to the breathing circuit. A venting valve may be provided to allow exhaled air to exit to the atmosphere.

The controller may be arranged to determine that the pressure signal is representative of breathing when the pressure signal comprises the characteristics of at least one inhalation event and at least one exhalation event within a predetermined period.

The controller may be arranged to determine that the pressure signal is representative of breathing when the pressure signal comprises the characteristics of at least two inhalation events and/or at least two exhalation events within the predetermined period.

The controller may be arranged to determine that the pressure signal is representative of breathing when the pressure signal sequentially comprises the characteristics of an inhalation event, an exhalation event, and an inhalation event within the predetermined period; or when the pressure signal sequentially comprises the characteristics of an exhalation event, an inhalation event, and an exhalation event within the predetermined period.

The predetermined period may be at least one tenth of a second, and may be at least two seconds.

The controller may be arranged to determine that the pressure signal comprises the characteristics of an inhalation event or an exhalation event when the pressure signal is indicative of a pressure change within the breathing circuit which corresponds to a depth of breathing which is at least one liter.

The controller may be arranged to determine that the pressure signal comprises the characteristics of an exhalation event when the magnitude of the pressure signal exceeds an upper threshold, and may be arranged to determine that the pressure signal comprises the characteristics of an inhalation event when the magnitude of the pressure signal falls below a lower threshold.

The controller may be arranged to determine that the pressure signal is representative of breathing when the pressure signal sequentially comprises a first pressure change that exceeds a pressure change threshold, a second pressure change that exceeds a pressure change threshold, and a third pressure change that exceeds a pressure change threshold. The first and third pressure changes may be pressure rises and the second pressure change may be a pressure fall. The first and third pressure changes may be pressure falls and the second pressure change may be a pressure rise. The controller may be arranged to determine that the pressure signal is representative of breathing when the second pressure change occurs within a preset time window following the first pressure change and when the third pressure change occurs within a preset time window following the second pressure change.

The pressure sensor may be an analogue pressure sensor, the controller being configured to convert the signal representative of the sensed pressure into a digital signal.

For a better understanding of the present invention, and to show more clearly how it may be carried into effect, reference will now be made, by way of example, to the accompanying drawings, in which.

Figure 1:
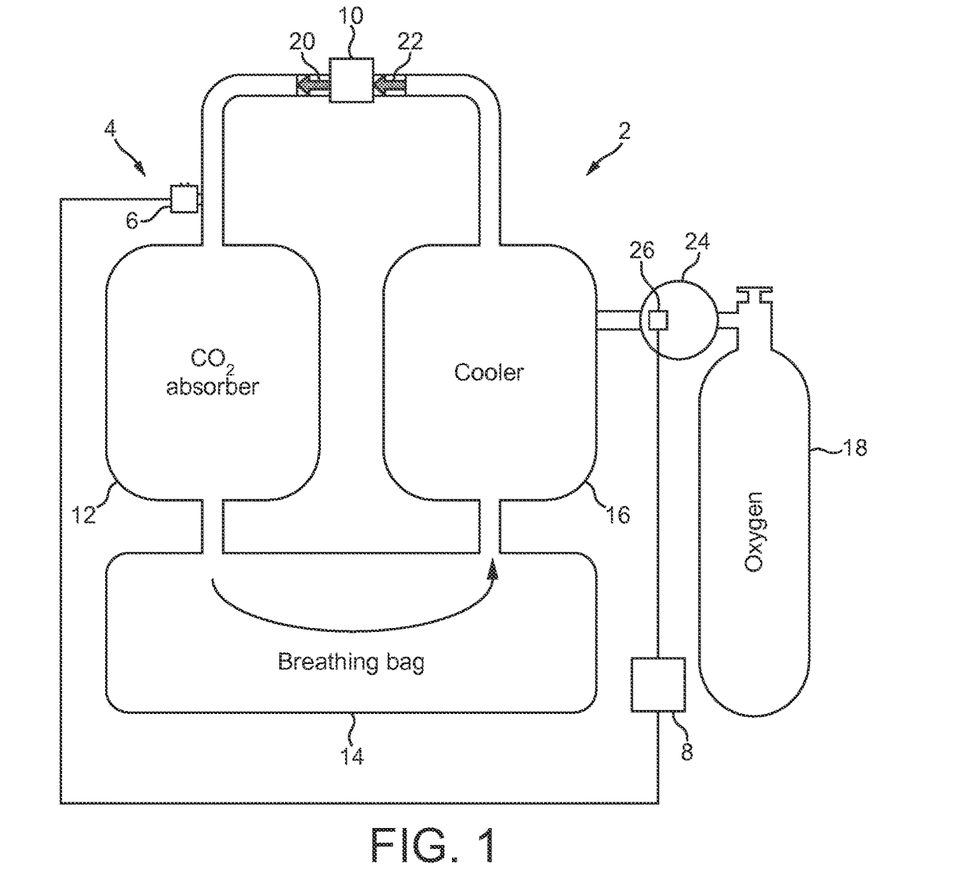
FIG. 1 is a schematic representation of a close circuit breathing apparatus.

FIG. 1 is a schematic representation of a closed circuit breathing apparatus 2 comprising a breathing circuit 4, a pressure sensor 6 arranged to sense pressure within the breathing circuit 4 and a controller 8 connected to the pressure sensor 6 for receiving a pressure signal from the pressure sensor 6. In this embodiment, the pressure sensor 6 is a static pressure difference sensor which outputs a pressure signal which represents a pressure difference between the pressure within the breathing circuit and the ambient pressure. The pressure sensor 6 may be a low-pressure pressure sensor capable of detecting pressure differences which are less than 1 bar.

The breathing circuit 4 comprises a breathing port 10, a carbon dioxide absorber 12, such as a scrubber, a counterlung 14 in the form of a variable volume breathing bag, and a cooler 16. An oxygen supply 18, for example a cylinder of compressed oxygen, is provided for supplying oxygen to the breathing circuit 4.

The pressure sensor 6 can be arranged to sense pressure at any suitable location within the breathing circuit 4. In the embodiment shown, the pressure sensor 6 detects a pressure upstream of the carbon dioxide absorber 12.

The breathing port 10, carbon dioxide absorber 12, counterlung 14 and cooler 16 are arranged in fluid communication with each other so as to define a closed loop which extends from the breathing port 10 through the carbon dioxide absorber 12, counterlung 14 and cooler 16 before returning to the breathing port 10. First and second non-return valves 20, 22 are disposed on opposite sides of the breathing port 10: the first non-return valve 20 being disposed between the breathing port 10 and the carbon dioxide absorber 12, and the second non-return valve 22 being disposed between the breathing port 10 and the cooler 16. The non-return valves 20, 22 are arranged such that air within the breathing circuit 4 flows in the anticlockwise direction (as shown in FIG. 1) only; that is, from the breathing port 10, through the carbon dioxide absorber 12, the counterlung 14 and the cooler 16 before returning to the breathing port 10.

The oxygen supply 18 is in fluid communication with the cooler 16 via a valve arrangement 24. The valve arrangement 24 can be opened and closed so that the oxygen supply to the breathing circuit 4 can be turned on or off. The breathing apparatus 2 is equipped with an oxygen sensor 26 for determining whether oxygen is being supplied to the breathing circuit 4. In this embodiment the oxygen sensor 26 is a pressure sensor that is disposed downstream of the cylinder valve. The oxygen pressure sensor 26 is connected to the controller 8 so that the output of the sensor 26 is inputted to the controller 8. If the pressure sensed by the oxygen pressure sensor 26 is above a threshold, which in this embodiment is 8 bar, it is determined that sufficient oxygen is being supplied to the breathing circuit. In other embodiments the oxygen sensor may comprise a device for determining whether the cylinder valve arrangement 24 is open or closed, or may comprise a pressure switch.

In normal operation, a user breathes through the breathing port 10. As the user exhales, air is forced through the first non-return valve 20, carbon dioxide absorber 12 and into the counterlung 14. The carbon dioxide absorber 12 absorbs a significant amount of the carbon dioxide which is present in the exhaled air. As the user inhales, air is drawn from the counterlung 14, through the cooler 16 and through the second non-return valve 22. As the air is drawn through the cooler 16 it mixes with the oxygen delivered to the cooler 16 by the oxygen supply 18. The oxygen supply 18 replenishes the air within the breathing circuit 4 with oxygen.

As the user inhales and exhales, the pressure within the breathing circuit 4 fluctuates. Each time the user exhales, the pressure within the breathing circuit 4 increases. As the user inhales, the pressure within the breathing circuit 4 decreases.

Figure 2:
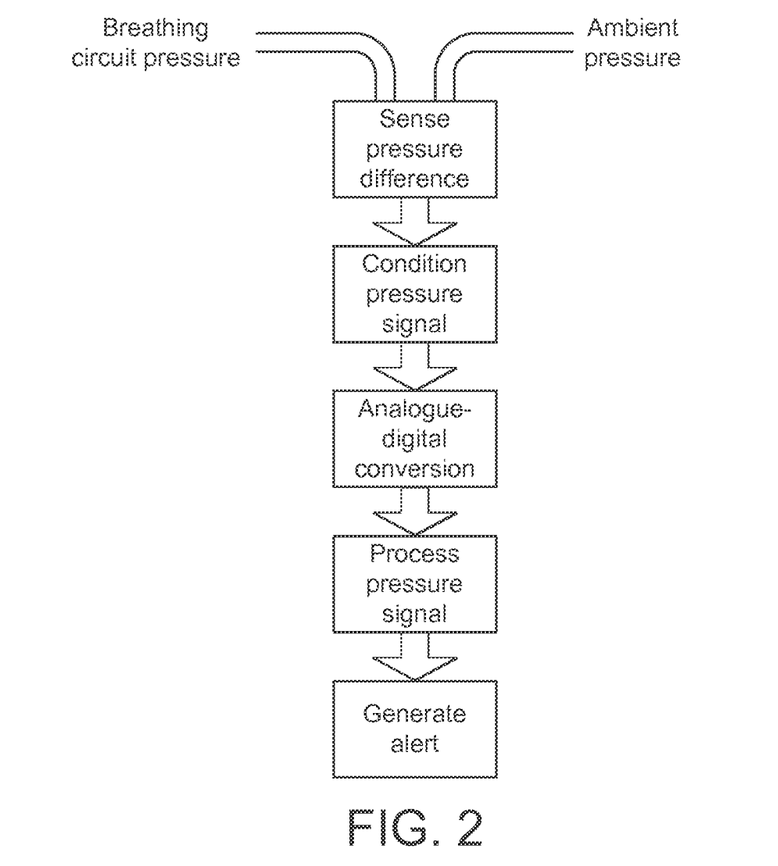
FIG. 2 schematically illustrates a method in which the controller of the breathing apparatus may operate.

With reference to FIG. 2, the pressure sensor 6 is arranged to sense a pressure difference between the pressure within the breathing circuit 4 and the ambient pressure of the atmosphere surrounding the breathing apparatus 2. The pressure sensor 6 outputs an analogue pressure signal to the controller 8. It should be appreciated that in other embodiments the pressure sensor 6 could be a digital pressure sensor. The pressure signal represents the pressure difference between the breathing circuit 4 and the ambient pressure. The pressure signal therefore varies in accordance with the variation in the pressure difference. The controller 8 conditions the signal, for example to remove noise and amplify the signal, and then converts the signal into a digital signal for further processing by the controller 8.

The controller 8 is arranged to determine if the pressure signal generated by the pressure sensor 6 is representative of breathing. This may be accomplished in one of a number of ways.

First Embodiment

In a first embodiment, the controller 8 determines if the pressure signal comprises the characteristics of a number of inhalation or exhalation events within a predetermined period of time. If the controller 8 determines that the pressure signal comprises an inhalation event, followed by an exhalation event, followed by an inhalation event within a predetermined period of time, the controller 8 determines that the pressure signal is representative of breathing.

Figure 3:
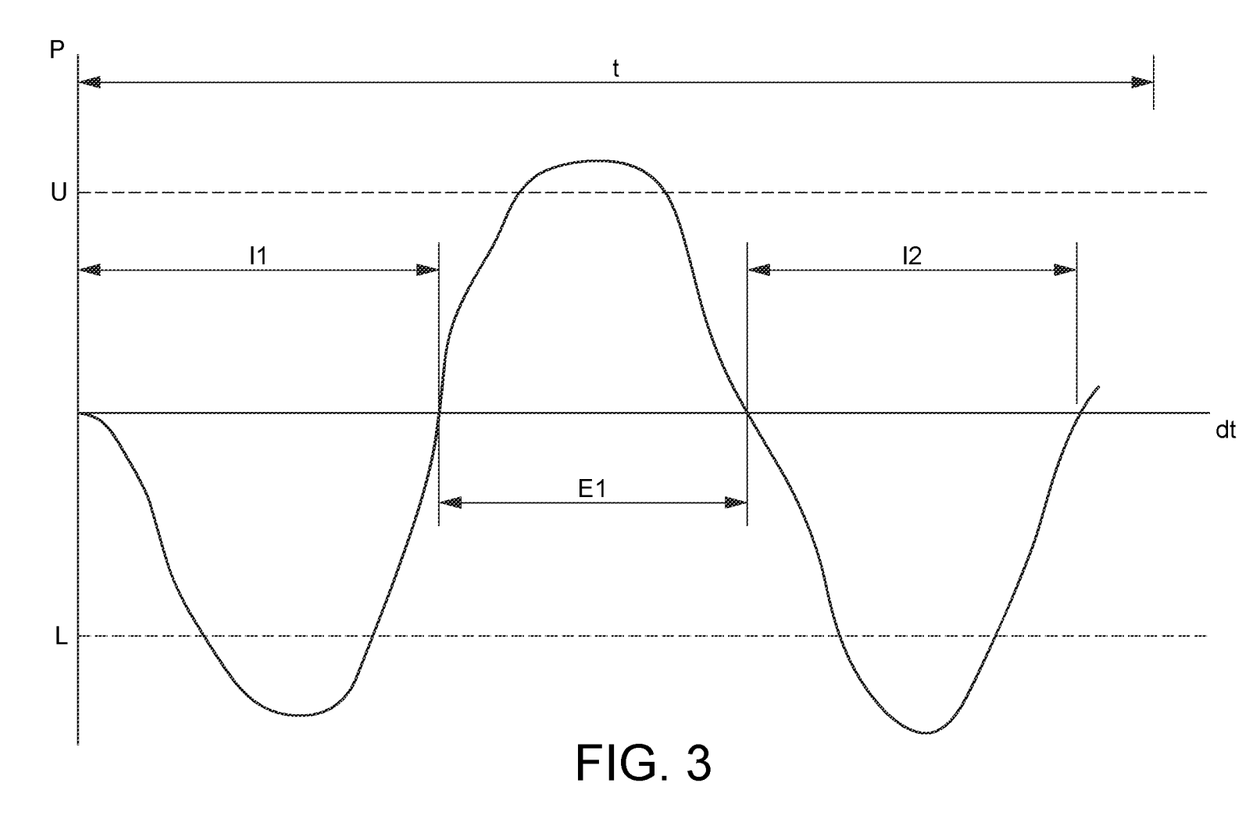
FIG. 3 schematically shows an example of an analogue output from a pressure sensor of the breathing apparatus of FIG. 1.

An example of a pressure signal that is representative of breathing is schematically shown in FIG. 3. The pressure signal comprises a negative spike (or pulse) I1 that is characteristic of an inhalation event, followed by a positive spike (or pulse) E1 that is characteristic of an exhalation event, followed by a second negative spike I2 that is characteristic of a second inhalation event. Since these three spikes or pulses I1, E1, I2 occur within the predetermined period of time t, the controller determines that the pressure signal is representative of breathing. The predetermined period of time t is set based on maximum time period within which a user would normally inhale, exhale and inhale again.

The controller may determine that inhalation has occurred if the pressure signal falls below a predetermined lower threshold value and may determine that exhalation has occurred if the pressure signal rises above a predetermined threshold value. The upper and lower threshold values are stored in a memory of the controller 8. The threshold values may be set at values which represent a pressure change within the breathing circuit that corresponds to a depth of breathing of at least 0.5 liters, OR at least 1 liter, for example. The upper and lower thresholds are indicated on the graphical representation of a pressure signal in FIG. 3 as U and L. As will be apparent to one skilled in the art, other analysis techniques may be used to determine inhalation and exhalation events.

If the pressure signal falls below the lower threshold value L, the controller 8 registers this as an inhalation event. The controller 8 continues to monitor the pressure signal. If the pressure signal subsequently exceeds the upper threshold value U within a predetermined period of time, the controller 8 registers this as an exhalation event. The controller 8 may at this stage determine that the pressure signal is representative of breathing.

In another arrangement, the pressure signal must subsequently fall below the lower threshold value L for a second time within the predetermined time period, which the controller 8 registers as a second inhalation event, before the controller 8 determines that the pressure signal is representative of breathing.

Determining that the pressure signal is representative of breathing only when the pressure signal has fallen below the lower threshold value (which is registered as inhalation), exceeded the upper threshold value (exhalation) and then again fallen below the lower threshold value (inhalation) reduces the likelihood of random fluctuations in ambient pressure causing a false determination of breathing. It will be appreciated that the controller may also determine that the pressure signal is representative of breathing when the pressure signal first exceeds an upper threshold value (exhalation), falls below a lower threshold value (inhalation) and again exceeds (exhalation) the lower threshold value.

The shorter the predetermined period of time, the greater the risk that slower breathing rates may not be detected. The predetermined period of time is therefore a period which ensures that breathing at expected rates can be detected. The predetermined period of time may, for example, be the maximum time taken to complete a full respiration cycle at the expected lowest rate of respiration.

The accuracy of the determination of breathing by the controller 8 can be improved by increasing the number of events in which the pressure signal alternately exceeds and falls below the threshold value before a positive determination that the pressure is representative of breathing is made. It will be appreciated that where the number of events required is increased a corresponding increase in the duration of the predetermined period is also made. It is expected that the specific embodiment described above in which three registered events are required for determination of breathing provides an acceptable certainty of detection of breathing without undue delay in detection time.

Second Embodiment

Figure 4:
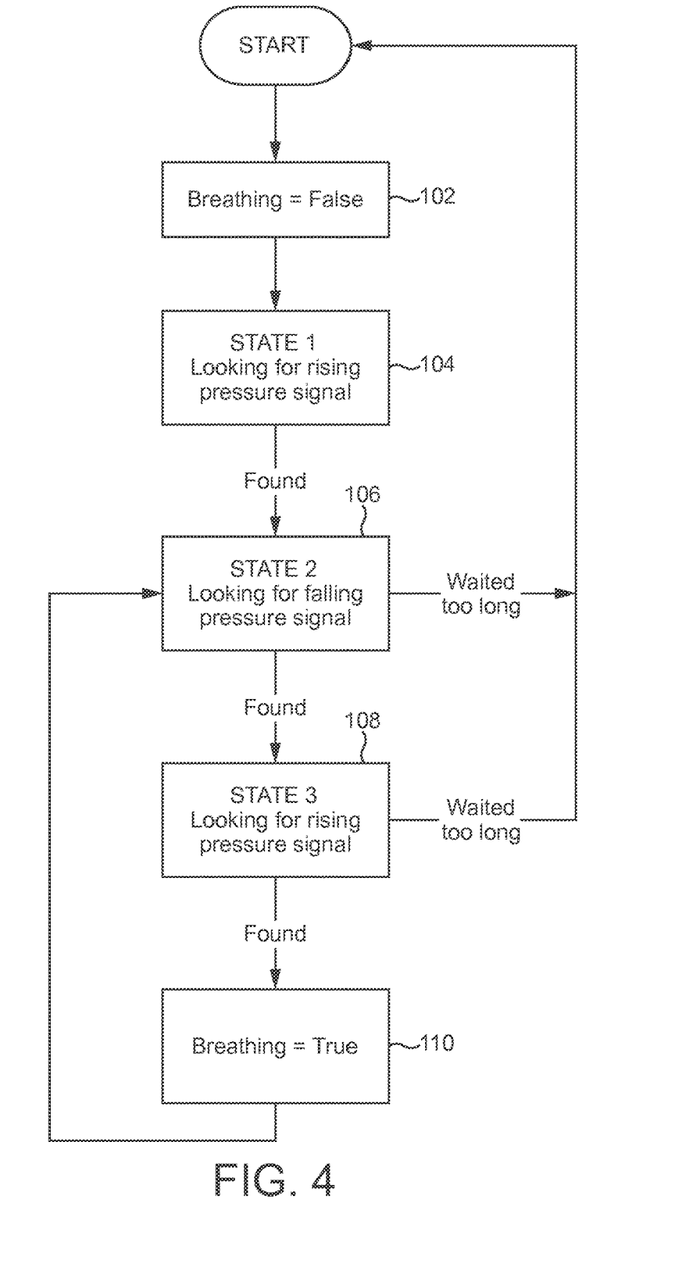
FIG. 4 shows a flow chart of a method of determining if the pressure signal is representative of breathing.

FIG. 4 shows a flow diagram of a method that may be used in a second embodiment to determine if the pressure signal is representative of breathing. In step 102 the controller 8 sets the breathing status as "false" to indicate that it has not detected a pressure signal that is representative of breathing. In step 104, the controller 8 is in STATE 1 in which it continually samples the pressure signal looking for a pressure rise ΔPr that exceeds a rising threshold. When this has been found, the controller 8 moves to step 106. In step 106, the controller 8 is in STATE 2 in which it continually samples the pressure signal looking for a pressure drop ΔPd that exceeds a falling threshold. If this pressure drop is not found within a preset time window tw the controller 8 returns to step 102 and resets the breathing status as "false". However, if the controller 8 finds the pressure drop ΔPd within the time window tw it moves to step 108. In step 108, the controller is in STATE 3 in which it continually samples the pressure signal looking for a pressure rise ΔPr that exceeds a rising threshold. If this pressure rise ΔPr is not found within a preset time window tw the controller 8 returns to step 102 and resets the breathing status as "false". However, if the controller 8 finds the pressure rise ΔPr within the time window tw it moves to step 110 in which it sets the breathing status as "true" to indicate that the pressure signal is representative of breathing.

The controller 8 then moves to step 106 in which it once again looks for a pressure drop ΔPd, followed by step 108 in which it looks for a pressure rise ΔPr. If at any point the controller 8 does not detect the required pressure drop ΔPd (in step 106) or rise ΔPr (in step 108) within the preset time window tw, it returns to step 102 and sets the breathing status as "false" to indicate that the pressure signal being detected is no longer representative of breathing.

The threshold pressure rise ΔPr and the threshold pressure drop ΔPd may be set such that they are normally only exceeded when breathing is occurring. The pressure rise and fall will depend on the overall volume of the breathing circuit. The time window tw is set such that when shallow breathing is occurring the next pressure rise or fall will be detected within the time window.

Figure 5:
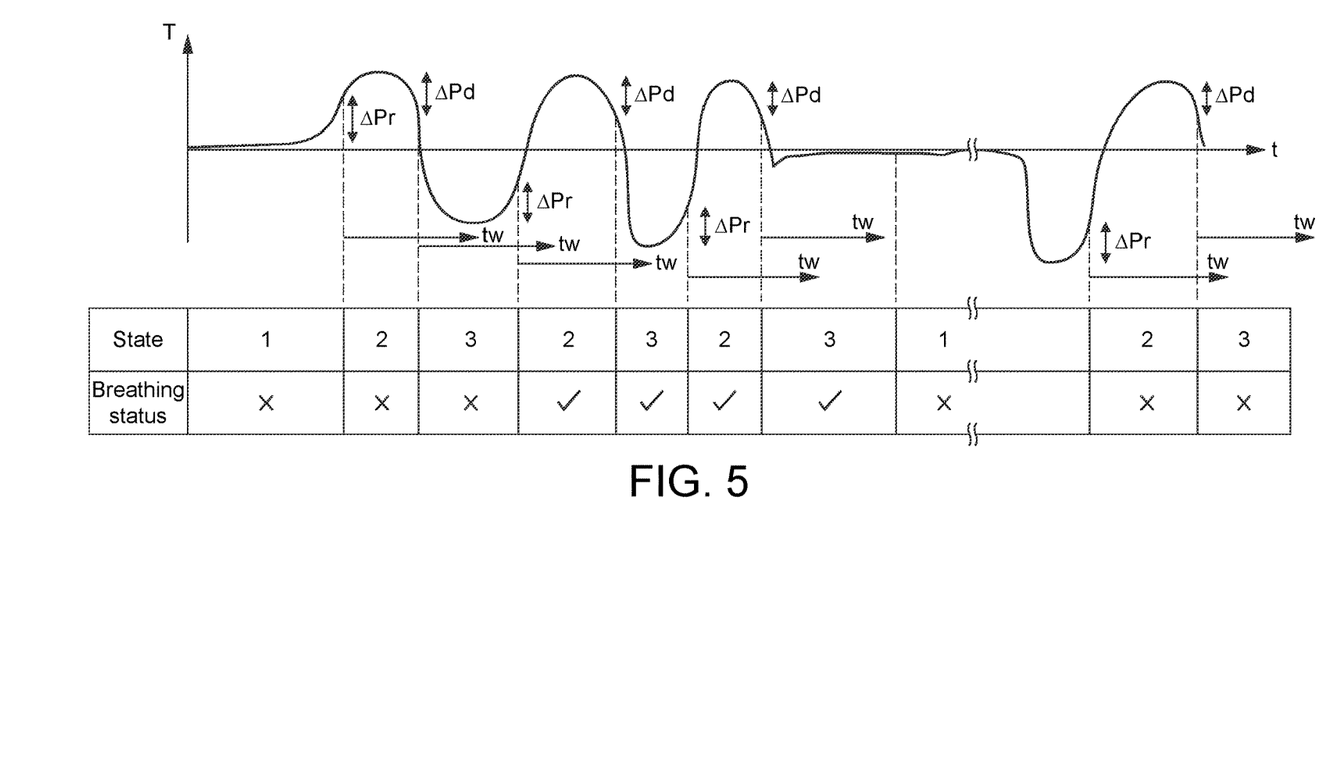
FIG. 5 schematically shows a pressure signal analysed by the method shown in FIG. 4.

This method is graphically illustrated in FIG. 5 which shows a pressure signal, the state the controller 8 is in, and the breathing status. As can be seen from FIG. 5, when the controller has detected a pressure rise ΔPr, a pressure drop ΔPd, and a pressure rise ΔPr, the breathing status is set as "true" to indicate that the signal is representative of breathing. When the controller does not detect the required pressure rise ΔPr within the time window tw, the breathing status is set as "false" to indicate that the pressure signal is no longer representative of breathing and the controller returns to STATE 1 in which it looks for a pressure rise ΔPr.

If it is determined by the controller 8 that the pressure signal is representative of breathing, an alert is generated if the oxygen pressure sensor 26 detects that sufficient oxygen is not being supplied to the breathing circuit 4. For example, if the controller 8 determines that breathing is occurring and the oxygen pressure sensor 26 detects that the pressure is less than 8 bar, an alert is generated. This alert may be audible or visual or vibratory, for example. This alerts the user who can respond by taking any remedial action that is required. For example, the user can check that the oxygen cylinder valve is open, check that the oxygen supply is properly connected, connect a new oxygen supply or check for faults with the breathing apparatus 2.

In an alternative embodiment, the controller 8 may be configured to turn on the oxygen supply if breathing is detected.

It will be appreciated that the controller 8 may monitor the pressure signal for a predetermined period of time after each inhalation or exhalation has been identified so as to ensure that any sequence of successive detected inhalations and exhalations are used to determine that the pressure signal is representative of breathing. The controller 8 may therefore conduct simultaneous independent analyses of the pressure signal for predetermined periods of time which overlap. This can be regarded as a "sliding window" analysis.

The invention claimed is:

1. A method of operating a closed circuit breathing apparatus having a closed breathing circuit from and into which a user breathes in use, the method comprising:
    determining whether a sufficient amount of oxygen is being supplied to the breathing circuit from a cylinder of oxygen;
    generating a time-varying pressure signal representative of the gas pressure within the breathing circuit;
    determining if breathing using the closed circuit breathing apparatus is occurring by determining whether the profile of the pressure signal generated is characteristic of a breathing pattern; and
    generating an audible, visual or vibratory alert only in response to the determination of both:
        (i) an insufficient amount of oxygen is being supplied to the breathing circuit, and
        (ii) breathing using the closed circuit breathing apparatus is occurring.

2. A method of operating a closed circuit breathing apparatus having a breathing circuit, the method comprising:
    determining whether a sufficient amount of replenishing gas is being supplied to the breathing circuit;
    sensing pressure within the breathing circuit using a pressure sensor;
    generating a pressure signal representative of the sensed pressure and the gas pressure in the breathing circuit;
    determining whether the pressure signal is representative of breathing; and
    generating and alert only in response to the determination of both an insufficient amount of replenishing gas is being supplied to the breathing circuit and that the pressure signal is representative of breathing.

3. A method as claimed in claim 2, wherein it is determined that the pressure signal is representative of breathing when the pressure signal sequentially comprises a first pressure change that exceeds a pressure change threshold, a second pressure change that exceeds a pressure change threshold, and a third pressure change that exceeds a pressure change threshold;
    wherein the first and third pressure changes are pressure rises and the second pressure change is a pressure fall; or wherein the first and third pressure changes are pressure falls and the second pressure change is a pressure rise.

4. A method as claimed in claim 3, wherein it is determined that the pressure signal is representative of breathing when the second pressure change occurs within a preset time window following the first pressure change and when the third pressure change occurs within a preset time window following the second pressure change.

5. A method as claimed in claim 2, wherein it is determined that the pressure signal is representative of breathing when the pressure signal comprises the characteristics of at least one inhalation event and at least one exhalation event within a predetermined period.

6. A method as claimed in claim 5, wherein it is determined that the pressure signal comprises the characteristics of an inhalation event or an exhalation event when the pressure signal is indicative of a pressure change within the breathing circuit which corresponds to a depth of breathing which is at least one liter.

7. A method as claimed in claim 5, wherein it is determined that the pressure signal comprises the characteristics of an exhalation event when the magnitude of the pressure signal exceeds an upper threshold.

8. A method as claimed in claim 5, wherein it is determined that the pressure signal comprises the characteristics of an inhalation event when the magnitude of the pressure signal falls below a lower threshold.

9. A method as claimed in claim 5, wherein it is determined that the pressure signal is representative of breathing when the pressure signal comprises the characteristics of at least two inhalation events and/or at least two exhalation events within the predetermined period.

10. A method as claimed in claim 9, wherein it is determined that the pressure signal is representative of breathing when the pressure signal sequentially comprises the characteristics of an inhalation event, an exhalation event, and an inhalation event within the predetermined period; or when the pressure signal sequentially comprises the characteristics of an exhalation event, an inhalation event, and an exhalation event within the predetermined period.

11. A closed circuit breathing apparatus comprising:
a breathing circuit;
a replenishing gas sensor for determining whether a sufficient amount of replenishing gas is being supplied to the breathing circuit;
a pressure sensor arranged to sense pressure within the breathing circuit, the pressure sensor being arranged to output a pressure signal which is representative of the sensed pressure, and representative of the gas pressure in the breathing circuit; and
a controller connected to the pressure sensor, the controller being arranged to determine whether the pressure signal is representative of breathing and to generate an alert only in response to the determination that both an insufficient amount of replenishing gas is being supplied to the breathing circuit and that the pressure signal is representative of breathing.

12. A breathing apparatus as claimed in claim 11, wherein the pressure sensor is an analogue pressure sensor and the controller is configured to convert the signal representative of the sensed pressure into a digital signal.

13. A method as claimed in claim 11, wherein the controller is arranged to determine that the pressure signal is representative of breathing when the pressure signal sequentially comprises a first pressure change that exceeds a pressure change threshold, a second pressure change that exceeds a pressure change threshold, and a third pressure change that exceeds a pressure change threshold;
wherein the first and third pressure changes are pressure rises and the second pressure change is a pressure fall; or wherein the first and third pressure changes are pressure falls and the second pressure change is a pressure rise.

14. A method as claimed in claim 13, wherein the controller is arranged to determine that the pressure signal is representative of breathing when the second pressure change occurs within a preset time window following the first pressure change and when the third pressure change occurs within a preset time window following the second pressure change.

15. A breathing apparatus as claimed in claim 11, wherein the controller is arranged to determine that the pressure signal is representative of breathing when the pressure signal comprises the characteristics of at least one inhalation event and at least one exhalation event within a predetermined period.

16. A breathing apparatus as claimed in claim 15, wherein the controller is arranged to determine that the pressure signal comprises the characteristics of an inhalation event or an exhalation event when the pressure signal is indicative of a pressure change within the breathing circuit which corresponds to a depth of breathing which is at least one liter.

17. A breathing apparatus as claimed in claim 15, wherein the controller is arranged to determine that the pressure signal comprises the characteristics of an exhalation event when the magnitude of the pressure signal exceeds an upper threshold.

18. A breathing apparatus as claimed in claim 15, wherein the controller is arranged to determine that the pressure signal comprises the characteristics of an inhalation event when the magnitude of the pressure signal falls below a lower threshold.

19. A breathing apparatus as claimed in claim 15, wherein the controller is arranged to determine that the pressure signal is representative of breathing when the pressure signal comprises the characteristics of at least two inhalation events and/or at least two exhalation events within the predetermined period.

20. A breathing apparatus as claimed in claim 19, wherein the controller is arranged to determine that the pressure signal is representative of breathing when the pressure signal sequentially comprises the characteristics of an inhalation event, an exhalation event, and an inhalation event within the predetermined period; or when the pressure signal sequentially comprises the characteristics of an exhalation event, an inhalation event, and an exhalation event within the predetermined period.

\* \* \* \* \*